(12) United States Patent
Solomon et al.

(10) Patent No.: US 11,320,411 B2
(45) Date of Patent: May 3, 2022

(54) AIR POLLUTION SENSOR TO MEASURE MAJOR CARBON COMPONENTS IN THE ENVIRONMENT

(71) Applicant: GOVERNMENT OF THE UNITED STATES AS REPRESENTED BY THE ADMINISTRATOR OF THE U.S. ENVIRONMENTAL PROTECTION AGENCY, Washington, DC (US)

(72) Inventors: Paul A. Solomon, Henderson, NV (US); Thomas Kirchstetter, Oakland, CA (US)

(73) Assignees: GOVERNMENT OF THE UNITED STATES AS REPRESENTED BY THE ADMINISTRATOR OF THE U.S. ENVIRONMENTAL PROTECTION AGENCY, Washington, DC (US); THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 644 days.

(21) Appl. No.: 16/288,925

(22) Filed: Feb. 28, 2019

(65) Prior Publication Data
US 2019/0277819 A1 Sep. 12, 2019

Related U.S. Application Data

(60) Provisional application No. 62/761,035, filed on Mar. 9, 2018.

(51) Int. Cl.
*G01N 21/3518* (2014.01)
*G01N 33/00* (2006.01)
*B01D 39/20* (2006.01)
*B01D 46/00* (2022.01)
*B01D 53/86* (2006.01)
(Continued)

(52) U.S. Cl.
CPC ....... *G01N 33/004* (2013.01); *B01D 39/2082* (2013.01); *B01D 46/0027* (2013.01); *B01D 46/62* (2022.01); *B01D 46/84* (2022.01); *B01D 53/8687* (2013.01); *G01N 21/3518* (2013.01); *G01N 33/0011* (2013.01); *B01D 2255/1021* (2013.01); *B01D 2255/1023* (2013.01); *B01D 2255/2073* (2013.01); *B01D 2258/06* (2013.01)

(58) Field of Classification Search
CPC ............ B01D 2258/06; B01D 53/8687; G01N 21/3518; G01N 15/0625; G01N 33/004; G01N 2015/0693; G01N 33/0011; Y02A 50/20
See application file for complete search history.

(56) References Cited

U.S. PATENT DOCUMENTS 3,922,551 A * 11/1975 Williams ........... G01N 21/3518
250/343
6,147,351 A * 11/2000 Huiku .................... G01N 21/61
250/343

(Continued)

*Primary Examiner* — Timothy C Vanoy
(74) *Attorney, Agent, or Firm* — Stein IP, LLC

(57) ABSTRACT

The invention relates to a device for measuring, in near-real-time, the level of black carbon, brown carbon, organic carbon, total carbon and $CO_2$ in air. The device also provides for a direct calculation of aerosol angstrom coefficient as well as estimation of emissions rates of black carbon or brown carbon from nearby combustion sources.

20 Claims, 1 Drawing Sheet

(51) Int. Cl.
*B01D 46/62* (2022.01)
*B01D 46/84* (2022.01)

(56) References Cited

U.S. PATENT DOCUMENTS

| | | | |
|---|---|---|---|
| 8,531,671 B1 * | 9/2013 | Hansen | G01N 1/2205 356/438 |
| 2001/0029775 A1 * | 10/2001 | Uchihara | G01N 15/0618 73/28.01 |
| 2011/0204236 A1 * | 8/2011 | Wong | G01N 33/004 250/340 |

* cited by examiner

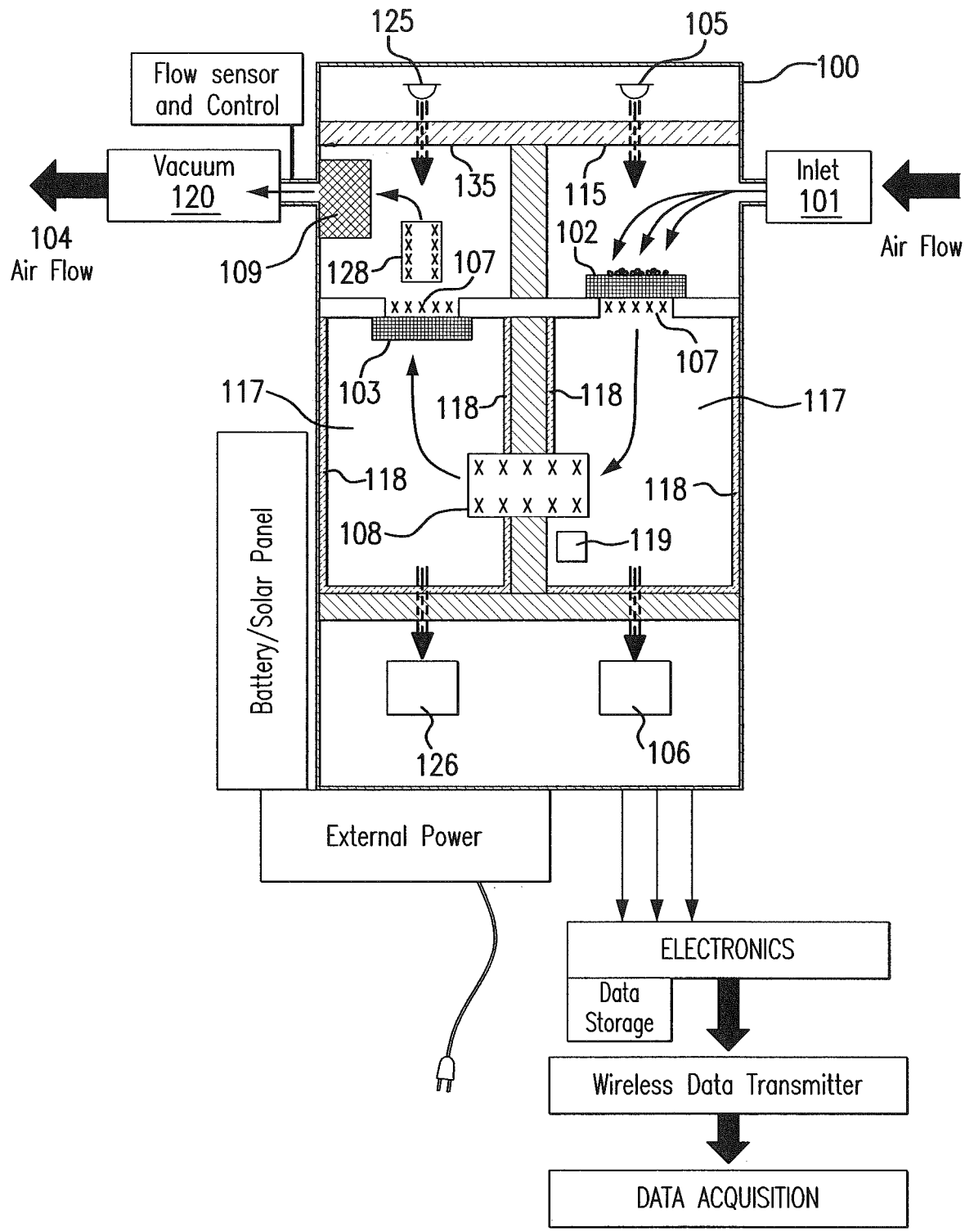

AIR POLLUTION SENSOR TO MEASURE MAJOR CARBON COMPONENTS IN THE ENVIRONMENT

CROSS-REFERENCE TO RELATED APPLICATIONS

This application claims the benefit of priority to U.S. Provisional Application No. 62/761,035, filed Mar. 9, 2018 in the U.S. Patent and Trademark Office. All disclosures of the documents named above are incorporated herein by reference.

BACKGROUND OF THE INVENTION

1. Field of the Invention

The invention relates generally to a device that measures, in real time, at least five contaminants and an optical aerosol property found in air, as well as fuel-based black carbon emission rates from nearby sources. Said contaminants include but are not limited to black carbon (BC), brown carbon (BrC), total carbon (TC), organic carbon (OC), and carbon dioxide ($CO_2$). The aerosol optical property is the aerosol angstrom coefficient, important for understanding climate change and visibility.

Black carbon and brown carbon are two of the most important light absorbing substances in the atmosphere. Chemically, black carbon is a component of fine particulate matter (PM≤2.5 micrometer (μm) in aerodynamic diameter (AD)). Black carbon is a complex component of particulate matter formed through the incomplete combustion of fossil fuels, biofuel, and biomass, and is emitted in both anthropogenic and naturally occurring soot. Black carbon is primarily released by high-temperature combustion.

Brown carbon, on the other hand, is brown smoke released by the incomplete combustion of fuels, especially during lower temperature combustion or pyrolysis. Brown carbon is emitted mainly by biomass combustion and is thus a source tracer for the incomplete combustion of wood.

Organic carbon is typically a major component (40-70%) of PM 2.5 (particles less than 2.5 micrometers (in diameter) in ambient air. It also is a complex mixture of many compounds that have natural and anthropogenic sources. Total carbon is the sum of organic carbon, black carbon, and brown carbon. Carbonate carbon is another type of carbonaceous material found in particulate matter, typically in particles greater than 3 μm in diameter with high amounts of soil dust related material, that might include windblown dust and construction dust, for example.

No single device or method currently exists that simultaneously measures levels of black carbon, brown carbon, and $CO_2$ in the air and also measures levels of total carbon, organic carbon. Moreover, no single device or method exists that simultaneously measures the concentration of these pollutants, provides direct calculation of the aerosol angstrom coefficient, and, as by direct calculation, measures fuel-based black carbon emission rates from sources in real- or near-real-time, at low cost, using a small form factor, and requiring low maintenance and low power. There is a need for a device with a form factor small enough to allow it to be portable and used in personal and mobile (surface and aloft) monitoring platforms as well in indoor and outdoor stationary locations. Such a device would be a significant advancement over previous attempts in this area that required human intervention to change filters and only measured black carbon. It is an objective of this invention to develop a device and method that addresses these needs.

SUMMARY OF THE INVENTION

Broadly speaking, the device of the invention is used to measure the level of $CO_2$ and particle phase carbonaceous components in air. The particle phase carbonaceous components in air measured by the device include black carbon, brown carbon, organic carbon and total carbon. The device provides for the simultaneous measurement of $CO_2$ and the particle phase carbonaceous components. The angstrom coefficient is calculated based on measures of absorption at two wavelengths.

The device of the invention may include the following components: an inlet for air to enter the device and limit the size of particles entering the device; an outlet for air to exit the device; a vacuum source to pull air into and out of the device; a first fibrous filter; a second fibrous filter; at least one light source; at least one light detector; a first heating element in thermal connection with the first fibrous filter and a second heating element in connection with the second fibrous filter; at least one heated oxidation catalyst; and a $CO_2$ detector. Additional components may include temperature, relative humidity, and pressure sensors, a source of power that can be a battery with or without recharge by connection to a solar photovoltaic device, or connection to an electrical AC outlet; wireless data transmitter; and electronics to convert voltage to a digital single.

The first fibrous filter and the second fibrous filter do not contain carbonaceous material, are configured to be heated to temperatures up to 1200° C., and are configured to filter and collect particulate matter from the air; the first fibrous filter and the second fibrous filter are positioned between the at least one light source and the at least one light detector; air is directed from the inlet through the first fibrous filter over the heated oxidation catalyst, through the second fibrous filter, (optionally) over a second heated catalyst, through the $CO_2$ detector, and through the outlet; the at least one light source directs light at preset wavelengths through the first fibrous filter and the second fibrous filter to the at least one light detector to detect the particle phase carbonaceous components in air.

The air entering the device may be indoor air or outdoor air. The device may be located in mobile (surface and aloft) or stationary platforms, and in in drones or other personal monitoring devices.

In one embodiment of the invention, the fibrous filter is made of quartz fiber, although the fibrous filter may be made of another material that has suitable properties.

In another embodiment of the invention, the oxidation catalyst is Pt, Pd, or a metal oxide (e.g., $MnO_2$). Catalysts of another material that can provide sufficient heat in the appropriate time may also be used.

In an embodiment of the invention, the inlet may comprise at least one of a size selective inlet and a light scattering sensor.

In an embodiment of the invention, the first fibrous filter and the second fibrous filter may be regenerated after particle collection by heating each filter to a temperature from about 500° C. to about 1200° C.

In another embodiment of the invention, carbonaceous gases evolved from regenerative heating of the first fibrous filter and/or the second fibrous filter pass over at least one heated oxidation catalyst and are converted to $CO_2$. Heating the second filter to evolve collected organic matter or particulate matter would occur 1) to evolve collected carbon that adsorbed or absorbed onto the second filter to account for the potential artifact or 2) if the flow were reversed and particulate matter were collected on the second filter and heated to measure the four particulate components of the particulate matter.

The device also may include a $CO_2$ detector (e.g., a nondispersive infrared sensor, a solid-state $CO_2$ detector, or other $CO_2$ detector (i.e., MEMS)) to measure the $CO_2$ as a means of measuring the total evolved carbon as well as a continuous measure of ambient $CO_2$ when the filter is not being flashed. In another embodiment with reverse flow, two $CO_2$ detectors may be used to measure evolved and ambient $CO_2$.

In an embodiment of the invention, the device includes a chamber that encompasses a first oxidation filter and the second fibrous filter, and the walls of the chamber are heated slightly above ambient temperature or are coated with a substance to reduce absorption of the evolved gas phase organics or $CO_2$.

In an embodiment of the invention, the at least one light source (e.g., a light emitting diode (LED) or other light source) is configured to emit light at a wavelength of 880 nm to measure the level of black carbon. At a wavelength of 880 nm, black carbon is the predominant particulate matter species to absorb light.

In another embodiment, the at least one light source is configured to emit light at a wavelength of 370 nm to measure the level of brown carbon. Light sources of other wavelengths may also be applied to measure the level of other particulate matter species.

In an embodiment of the invention, the device further includes a relative humidity sensor, pressure sensor, and a temperature sensor, which may be mounted directly in the air sample flow path between the sample and reference photodiodes. In this embodiment, the first fibrous filter is configured to filter particulate matter and the second fibrous filter is configured to serve as a reference filter to approximate changes in optical transmission of the first filter due to conditions other than the effect of the collected particulate matter (e.g., to compensate for changes in temperature, pressure, and relative humidity). The device may also include a pressure sensor.

The at least one light detector used in the device of the invention may be a photodiode to measure transmitted light at one or multiple wavelengths to determine the level of black carbon, brown carbon, or other light absorbing components. Photodiodes generate electrical voltages that are proportional to the intensity of light transmitted through each filter. Multiple photodiodes or other types of light detectors may also be used.

The analog voltage measurements from the photodiodes may be digitized using a 24-bit analog-to-digital (ADC) converter and processed by a microcontroller unit (MCU).

In an embodiment of the invention, a differential pressure sensor or other suitable airflow measuring device (e.g., MEMS flow sensor) is installed downstream of the device housing to measure the volumetric flow rate of the sampled air. The MCU may generate a pulse-width modulated signal to control the electrical power delivered to a rotary vane pump or other vacuum source and maintain a desired flow rate between about 5 and 500 cc/minute.

In an embodiment of the invention, the inlet for air to enter the device may include an ancillary device to remove particles larger than a specific size (e.g., cutpoint of 2.5 µm aerodynamic diameter, AD), allowing only particles less than that size to enter the device. A range of sizes are applicable including sizes that limit particles entering the device to, for example, below 0.3 µm AD, 0.5 µm AD, 1 µm AD, 4 µm AD, 10 µm AD). The ancillary device may have a collection efficiency of about 50% at the desired cutpoint.

In an embodiment of the invention, the inlet for air to enter the device may include a device to measure particle light scattering (e.g., a light scattering sensor) that provides an estimate of the mass concentration of particulate matter, and the particulate matter and black carbon mass concentrations together are used to estimate the BC/PM ratio and the aerosol single scattering albedo (SSA). SSA is a ratio equal to the amount of light PM scatters to the amount of light PM extinguishes, different from extinction, which is the sum of scattering and absorption. An estimate of the SSA can be calculated from the BC/PM ratio by assuming published values of absorption and scattering cross-sections apply to the PM and BC. This device may be placed after the inlet that allows particles of a specific size to enter the device or it may be placed by itself with no size discrimination of particles entering the device.

In another embodiment of the invention, the device further includes one or more accessory devices for flow measurement and flow control.

In another embodiment of the invention, the device further includes one or more of a battery or a solar panel, which may be used if line power is not available.

In another embodiment of the invention, the device further includes electronics to collect, process, and transmit the collected signal wirelessly (radio or other wireless transmitter) or download the signal to an internal data storage source.

In another embodiment of the invention, the device further includes software to convert the signal from voltage to absorption units (1/M or 1/Megameters) or to mass concentration in micrograms per meter cubed ($\mu g/m^3$), parts per million (ppm), or other units as is standard practice in this field.

In another embodiment of the invention, the device provides for direct calculation of the aerosol angstrom coefficient and supports the calculation of emission rates (e.g., grams of black carbon emitted per kilogram of fuel burned), the latter when nearby sources are present.

In an embodiment of the invention, separate light sources at preset wavelengths paired with light detectors, emit light directed through the first fibrous filter and the second fibrous filter, respectively, to detect specific contaminants and aerosol optical properties in air and allow for calculation of emissions rates into air from nearby sources.

One feature of the device of the invention is that it infrequently requires human intervention and down time to change filters (e.g., once per year). Rather, the device of the invention relies on heating the fibrous filters at temperatures between 500 and 1200° C. to eliminate collected particulate matter and regenerate the filter.

In another embodiment, the device of the invention is configured to simultaneously measure the levels of black carbon, brown carbon, total carbon, organic carbon (TC minus BC equals OC in units of $\mu g/m^3$), and $CO_2$, and allowing for a direct calculation of the aerosol angstrom coefficient. In the presence of nearby emissions sources, emissions rates from such nearby source(s), may be calculated simultaneously in the air.

In an embodiment of the invention, the small form factor of the invention allows for a size of the optical cell, for example, of about 6 cm×4 cm×1 cm. Larger and smaller sizes may result depending on the final design of the device.

BRIEF DESCRIPTION OF THE DRAWINGS

The invention is more fully described by reference to the following detailed description and the accompanying drawings.

FIG. 1 is a cross-sectional view of an embodiment of a device to measure the levels of black carbon, brown carbon, organic carbon, total carbon, and $CO_2$ as well as determine the aerosol angstrom coefficient and emissions rates from nearby sources.

DETAILED DESCRIPTION OF THE INVENTION

The flexible, low-cost, low-power, portable, wired or wireless, real-time sensor and device of the invention may have significant impact as to how EPA, other government agencies, and the public measure the major carbonaceous components and $CO_2$ in air across a wide array of situations. For example, EPA can employ this sensor at their National Ambient Air Quality Sites (NAAQS), near-roadway sites, and other air quality sites to measure the four carbonaceous fractions in particulate matter and $CO_2$ at very low cost, thus gaining a better understanding of the impact of these potentially harmful pollutants on public health, global warming, and regional climate change. EPA and other government agencies can ubiquitously distribute these sensors in many locations to measure black carbon, brown carbon, total carbon, organic carbon, and $CO_2$, filling in spatial and temporal gaps that exist in current air sampling networks.

This sensor and device of the invention may be used, for example, to better understand the spatial and temporal distribution and individual and community exposures of black carbon, brown carbon, total carbon, organic carbon, and $CO_2$ to the nearly 3 billion people worldwide that use individual indoor and outdoor cookstoves burning biomass fuel and coal. Within the US, old home heating stoves that produce very high levels of indoor pollution are prevalent in Indian Tribal communities. Thus, the sensors may be used to educate individuals and communities on the advantages of stove replacements that would improve the health within US Tribal nations and internationally. Agencies may deploy the sensors of the invention in aircraft and on balloon platforms and drones to better understand the vertical distribution of carbonaceous components in PM and $CO_2$ as well as the aerosol angstrom coefficient at high time resolution needed to understand transport of these pollutants supporting global climate change research. The sensors of the invention also may be deployed on or in mobile (surface and aloft) and stationary platforms to better understand personal exposure on and near roads and throughout communities. The public may use these sensors to measure their own exposures, indoors and outdoors, to help minimize their risk to these potentially harmful pollutants at the personal and community level especially in Environmental Justice areas. The sensor may also be applied within a personal monitor. Millions of these sensors could be distributed and data networked through a wireless interface into the Cloud followed by cloud computing and near real-time evaluation of personal, local, regional, and global scale variability in space and time of these pollutants. There is currently a need for a low-cost, low power, portable carbonaceous particulate matter sensor in the fast-growing commercial low-cost sensor market, which this invention will fulfill.

The device of the invention is designed to collect atmospheric particulate matter on a fibrous filter that does not contain carbonaceous material and has the capacity to be heated to a temperature as high as 1200° C.

One important feature of the device of the invention is that human intervention infrequently will be required to maintain and change the filters. Removing accumulated carbon and particulate matter from the filters is a cumbersome, expensive task that results in device downtime and, with a large number of sensors, considerable human resources and expense. The inventors have developed a system to remove the carbon and particulate matter in situ while the device is collecting data. More specifically, the device of the invention is adapted to thermally regenerate the fibrous filters by heating them to temperatures between 500 and 1200° C. This eliminates collected carbon and particulate matter during device operation.

In one embodiment of the invention, the fibrous filters used in the device are made of quartz-fiber (e.g., a Pallflex® Tissuquartz™ Filters, 2500 QAT-UP). The transmission of light through the filters is measured as discussed in more detail below. Decreasing light transmission through the filter due to the accumulation of carbon-based particulate matter will be converted to the mass concentration of black carbon collected on the filter (expressed in terms of mass of black carbon collected per $cm^2$ of filter material through which the air was drawn):

$$BC = ATN/\sigma$$

where:

BC is the mass concentration of black carbon collected on the filter in units of grams of black carbon per square centimeter ($g/cm^2$) of filter.

ATN stands for attenuation equal to ln(T), where T is transmission defined as $I(t2)/I(t1)$, where I is measured light intensity and t1 and t2 refer to the start and end of a measurement time period.

Sigma ($\sigma$), in units of $cm^2/g$ is a calibration factor that relates measured ATN to BC mass concentration.

ATN measured in the near infrared range (e.g., at 880 nm wavelength) is specific to detecting the presence of black carbon. ATN measured in the near ultraviolet range (e.g., 370 nm wavelength) is used to determine the presence of light absorbing organics, which are present in biomass and other smoke. The device of the invention is configured so that any wavelength between 200 nm and 1200 nm may be viable to measure other light absorbing components of PM for this application.

Periodically (e.g., hourly, daily, weekly) the filter may be regenerated by heating to remove the collected particulate matter, particularly the carbonaceous material collected on the filter. This may be accomplished by heating to temperatures greater than 500° C. but not exceeding 1200° C., whereupon the collected particulate matter is removed by evaporation and combustion. The evolved carbonaceous gases may then pass over a catalytic material (that also may be heated) and be converted to carbon dioxide, which in turn may be quantified using a $CO_2$ detector, including but not limited to an infrared detector. This will measure the levels of total carbon after conversion of all the carbon on the filter to $CO_2$, which may be expressed in terms of mass of carbon as typically performed in this field for the measurement of organic and black carbon by thermal methods from $CO_2$. Organic carbon is then estimated as the difference between total carbon (in units of, for example, $\mu g/m^3$) and black carbon (e.g., in $\mu g/m^3$).

Organic carbon artifact which results from absorption of organic gases in air on the quartz-fiber filter may be accounted for in the device of the invention by employing one or more approaches that involve controlling sampling time, using a special heating protocol, or separately flash heating the second filter that is configured to collect only sorbed organic gases. The evolved $CO_2$ from the second filter is then measured, converted to concentration ($\mu g/m^3$), and subtracted from the OC value of the first filter as described above for the first filter.

The device of this embodiment of the invention provides for sampling of particulate matter in ambient air (indoors or outdoors) by pulling air into the device and through the first and second fibrous filters using a small vacuum source. The vacuum source may be located downstream of both filters and also may be located downstream of the $CO_2$ detector and flow measuring device (see FIG. 1). The vacuum source may be, for example, a small rotary vane pump or other device which is suitable for moving air through the device.

In one embodiment of the invention, black carbon may be measured using a light source that emits light at 880 nm wavelength and measurement of the transmitted light at same wavelength to determine the absorption due to black carbon collected on the filter.

In another embodiment of the invention, brown carbon may be measured using a light source that emits light at, for example, 370 nm wavelength, in a similar fashion as described above.

In one embodiment of the invention, the device also provides for the use of wavelength measurements within the range of 200 nm and 1200 nm to more completely characterize how particulate matter absorbs light over this spectral range and potentially account for other absorbing species.

In an embodiment of the invention, the device provides for regeneration or cleaning of the first filter at temperatures above 500° C. and perhaps as high as 1200° C. in air (21% oxygen) to remove all carbonaceous material from the filter.

The fibrous filters used in the device of the invention may be heated to 1200° C. using a heating element (e.g., a metal alloy, such as NiCr or FeCrAl) either embedded within the fiber matrix or located above or below the fiber matrix. The heated fibrous filters are used to flash heat the collected particulate matter and evolve organic gases for the measurement of total carbon and organic carbon.

An embodiment of the claimed invention uses a heated (e.g., 50° C.-200° C., or other higher temperature) metal (e.g., Pt or Pd), metal oxide (e.g., $MnO_2$) catalyst, or other material catalyst that may provide sufficient heat in the appropriate time to oxidize the organic carbon evolved during regeneration and convert those carbonaceous gaseous compounds to $CO_2$. The catalyst design may include but not be limited to a packed bed, a single tube or series of tubes, a honeycomb shape, a screen, or parallel plate design.

In one embodiment of the invention, the device uses a $CO_2$ detector (e.g., an NDIR detector) and detection method to measure the $CO_2$ evolved during filter regeneration. This also provides a continuous measure of $CO_2$ concentrations in air when not measuring the evolved $CO_2$. The ambient concentration is measured as well to provide the baseline $CO_2$ concentration from which the evolved $CO_2$ is determined, since $CO_2$ is present in air.

In another embodiment of the invention, the device provides for heating the chamber walls between the first fibrous filter and the $CO_2$ detector to slightly above ambient (e.g., 1-3° C.) to reduce absorption of the evolved organic gases or $CO_2$ on the walls of the chamber located prior to the $CO_2$ measurement. In another embodiment, the wall may be coated with a material that will not absorb $CO_2$ reducing the amount of energy needed to operate the sensor.

An embodiment of the invention employs a second fibrous filter located downstream of the first fibrous filter in part to measure the absorption through the second filter using the same wavelength(s) as the first filter. This approach is designed to account for changes in the light source, detector, or other electronic components due to changes in temperature, pressure, and relative humidity observed within the sensor during sampling.

In another embodiment, the device of the invention includes at least one of a temperature sensor, a pressure sensor and a relative humidity sensor located either inside or immediately outside the device and within the exit flow of air from the device. Measurements of pressure, temperature and relative humidity may be used to compensate for changes caused by these parameters as needed, including for calculations of ambient concentration in mass per volume ($\mu g/m^3$) when used at elevations other than sea level and conversion to standard temperature and pressure are desired.

In an embodiment, the invention includes a flow sensor and flow controller to measure and control the flow rate through the sensor. The flow controller maybe be used to maintain a constant flow rate during sampling, typically using a feedback mechanism between the flow sensor and vacuum source. Other approaches may be used. The mass concentration is then calculated in the standard way knowing the volume (flow rate times time (measured as t2 minus t1)), the mass per square centimeter measured ($\mu g/cm^2$), and the collection area ($cm^2$) of the filter.

An embodiment of the invention also accounts for the potential of the gas phase absorption or adsorption artifact on the first filter by separately flash heating the second filter (which only sees particle free air, as the particles are removed by the first filter), oxidizing the evolved organic gases to $CO_2$, similar to the regeneration step above, and measuring the artifact similar to how total carbon is measured per the method indicated above. The assumption is that the absorption or adsorption on the second filter is similar to the first. In this embodiment, there may be two thermal oxidizing catalysts, a second thermal oxidizing catalyst located after the second filter (FIG. 1). The catalyst is followed by the $CO_2$ detector, flow control and flow sensor, and vacuum source.

In another embodiment of the invention, the method of estimating the organic artifact includes heating the first filter initially to 100° C. (not to exceed 130° C.) to drive off the low temperature carbon compounds, a majority of which are sorbed organic gases, and either measuring the mass of low temperature carbon or artifact carbon as described above (i.e., by oxidizing to $CO_2$ and detecting the sorbed gas phase carbon with the $CO_2$ detector), or by following the initial low-temperature heating by flash heating as described above. In the latter case, the low temperature organic carbon artifact has been removed first, leaving only collected particle carbon when flashed to high temperature. In the former case, the mass of the organic sampling artifact determined may be used to correct the total organic carbon and organic carbon particulate matter mass.

In an embodiment of the invention, the pressure is compensated for to reflect reduced pressures at higher elevations. For example, this may occur when the device is used at locations of higher elevation (e.g., Denver, Colo.), or when used in an aircraft, or aboard balloons, drones, or other aloft measurement platforms. Data from the temperature and pressure sensors can be used to convert the volume and thus mass concentration to standard temperature and pressure (STP).

Thermal regeneration of the device's filter, using quick heating to remove or "flash-off" collected particulate matter, allows the same filter to be used repeatedly over a long period of time, vastly extending the period of autonomous operation.

In an embodiment of the invention, the device allows for simultaneous measurement of optical ATN to measure carbon components that sorb at one or more wavelengths (e.g., 880 nm–BC; 370 nm–BrC) in a small form factor. The device also allows for simultaneous measurement of carbon that sorb light at multiple wavelengths between 200 nm and 1200 nm to potentially account for other components of particulate matter.

In another embodiment of the invention, the device also provides for chemical conversion of thermally evolved carbonaceous material to carbon dioxide over a heated catalyst and subsequent measurement of carbon dioxide, along with the optical measurement of black carbon, which allows for quantification of total carbon and, by difference, organic carbon (i.e., organic carbon equals total carbon minus black carbon).

In another embodiment of the invention, the device allows for automatic correction for the "organic carbon positive sampling artifact" that results from sorption of organic vapors to fibrous material.

One embodiment of the invention includes a filter for this small form factor device that includes a heating element (mesh, wire, or other) embedded in, under, or above the filter matrix, which allows the filter to undergo flash-heating to temperatures not to exceed 1200° C.

In another embodiment of the invention, the device also allows for integration of a method to convert organic gases evolved during the regeneration process into $CO_2$ with a detection method for $CO_2$ to allow for the measurement of total organic carbon, and thus by difference OC which is equal TC minus BC.

The real-time measurement of BC and BrC along with $CO_2$ allows for the determination of emissions rates (expressed in terms of, e.g., mass of BC or BrC emitted per mass of fuel burned) for nearby sources, for example by comparing the relative increases in BC and BrC to the relative increase in $CO_2$ above background concentrations, and using a carbon balance to relate above background $CO_2$ to the amount of fuel burned by the emitting source.

Turning to the drawings, FIG. 1 shows a cross-sectional view of an embodiment of the device of the invention. A vacuum source (120) pulls air into the device (defined by housing 100) through an inlet 101. The air then proceeds through a first fibrous filter 102, which filters particulate matter from the air. Particle free air is then directed through a second fibrous filter 103, which functions as a reference to which light passing through the particulate-laden, first fibrous filter is compared to determine the levels of black and (separately) brown carbon in the air. From there, the air is drawn through the air outlet 104 to exit the device.

At least one light source 105 (e.g., one or more light emitting diodes (LED)) is configured to emit light through window 115 at preset wavelengths through the first fibrous filter 102, and at least one light source 125 is configured to emit light through window 135 at the same preset wavelengths at the second fibrous filter 103. Light detectors (e.g., photodiodes) 106 and 126 are used to convert light transmission through the first fibrous filter to a voltage that can subsequently, through the electronics (MCU), be converted to the mass concentration of collected black carbon or brown carbon. Light is emitted from at least one light source at 880 nm to measure the level of black carbon. Light is emitted from at least one light source at 370 nm to measure the level of brown carbon. Other wavelengths may be used to measure other components of carbon or particulate matter.

The first fibrous filter and the second fibrous filter are regenerated by heating, using resistive heating element 107. The regeneration occurs at a temperature between 500° C. and 1200° C. The evolved carbonaceous gases are passed over a first oxidation catalyst 108 (heated in this embodiment) to convert the gases to carbon dioxide, which in turn is quantified using a $CO_2$ detector 109. The first oxidation catalyst is optional (i.e., not heated or removed) if only BC and BrC are to be measured.

A second oxidation catalyst 128 is located in the flow stream after second fibrous filter 103, which is also heated to convert the gases to carbon dioxide, which is also quantified using $CO_2$ detector 109. Heater 118 is used to heat the walls of chamber 117. Temperature, relative humidity and pressure sensors (119) are housed inside chamber 117. A flow sensor and control system may also be present at the flow outlet. Additional features either connected or appended to the device include a battery or solar panel as well as an external power outlet. The device is also configured to be connected to relevant data acquisition, data storage and wireless data transmission devices.

No single device or single method to date measures black carbon, brown carbon, total carbon, organic carbon, $CO_2$, and absorption angstrom exponent simultaneously, including larger more expensive instruments. The advantages of the new device are low cost, portability, small size, low power, and wireless communications providing data in near-real time for the four major carbonaceous components and $CO_2$ in air (indoor, outdoor, near emissions sources) within a widely distributed network including mobile (surface and aloft), stationary, and personal platforms. Use of this device will allow communities and individuals to reduce their risk to these pollutants.

The nearly real-time nature of the device allows for determination of BC and BrC pollutant emissions rates as in standard practice when near emissions sources. The use of multiple wavelengths to measure absorption at different wavelengths allows for the direct calculation of the aerosol angstrom coefficient as in standard practice—a measure of how light absorption varies with wavelength over the span of wavelengths. This is important for understanding the impact of aerosols on climate change and visibility.

As the present invention may be embodied in several forms without departing from the spirit or essential characteristics thereof, it will be understood that the invention is not limited by the details of the foregoing description, unless otherwise specified, but rather should be construed broadly within its spirit and scope as defined in the appended claims, and therefore all changes and modifications that fall within the metes and bounds of the claims. Accordingly, the invention is defined by the appended claims.

Although a few embodiments of the present invention have been shown and described, it would be appreciated by those skilled in the art that changes may be made in this embodiment without departing from the principles and spirit of the invention, the scope of which is defined in the claims and their equivalents.

The invention claimed is:

1. A device for measuring the level of $CO_2$, particle phase carbonaceous components, and the absorption angstrom coefficient in indoor and outdoor air, the device comprising:
   an inlet for air containing particles to enter the device;
   an outlet for air to exit the device;
   a vacuum source to draw air into and out of the device;
   a first fibrous filter;
   a second fibrous filter;
   at least one light source;
   at least one light detector;
   a first heating element in thermal connection with the first fibrous filter and a second heating element in connection with the second fibrous filter;

at least one heated oxidation catalyst; and
a $CO_2$ detector;
wherein the first fibrous filter and the second fibrous filter are not made of carbonaceous material and are configured to be heated to temperatures up to 1200° C.; the first fibrous filter is configured to collect particulate matter and gas phase organics from the air; the second fibrous filter is configured to collect approximately the same amount of gas phase organics from the air to account for artifact gas phase organics that are collected by the first filter; the first fibrous filter and the second fibrous filter are positioned between the at least one light source and the at least one light detector; air is directed from the inlet through the first fibrous filter, over the at least one oxidation catalyst, through the second fibrous filter, to a $CO_2$ detector, and through the outlet; the at least one light source directs light at preset wavelengths through the first fibrous filter and the second fibrous filter to the at least one light detector to detect the particle phase carbonaceous components in air.

2. The device of claim 1, wherein the particle phase carbonaceous components in air measured by the device comprise black carbon, brown carbon, organic carbon and total carbon.

3. The device of claim 2, wherein the levels of $CO_2$, absorption angstrom coefficient, black carbon, and brown carbon, are measured simultaneously.

4. The device of claim 1, wherein the inlet comprises at least one of a size selective inlet and a light scattering sensor.

5. The device of claim 1, wherein the first fibrous filter and the second fibrous filter are made of quartz fiber.

6. The device of claim 5, wherein the first fibrous filter and the second fibrous filter are configured to be regenerated by heating each filter to a temperature from about 500° C. to about 1200° C.

7. The device of claim 6, wherein the at least one oxidation catalyst comprises two oxidation catalysts, the second oxidation catalyst located so the flow of air is directed to the second oxidation catalyst after passing through the second fibrous filter.

8. The device of claim 7, wherein carbonaceous gases evolved from regenerative heating of the first fibrous filter and the second fibrous filter pass over at least one heated oxidation catalyst and are converted to $CO_2$, and the $CO_2$ detector measures the evolved $CO_2$ as an indirect measure of the carbon that was collected on the filters.

9. The device of claim 8, wherein the device comprises a chamber that encompasses the second fibrous filter and the at least one oxidation chamber, and the walls of the chamber are heated above ambient temperature or are coated with a substance to reduce absorption of the evolved gas phase organics or $CO_2$.

10. The device of claim 1, wherein the $CO_2$ detector is a nondispersive infrared sensor, a solid-state infrared detector, or MEMS detector.

11. The device of claim 1, wherein the at least one light source is configured to emit light at a wavelength of from 200 to 1200 nm.

12. The device of claim 11, wherein the at least one light source is configured to emit light at a wavelength of about 880 nm to measure the level of black carbon.

13. The device of claim 11, wherein the at least one light source is configured to emit light at a wavelength of about 370 nm to measure the level of brown carbon.

14. The device of claim 1, further comprising a relative humidity sensor, pressure sensor, and a temperature sensor.

15. The device of claim 14, wherein the first fibrous filter is configured to filter particulate matter and the second fibrous filter is configured to compensate for changes in temperature, pressure, and relative humidity.

16. The device of claim 1, wherein the at least one light detector is a photodiode.

17. The device of claim 16, wherein the photodiode generates electrical voltages that are linearly proportional to the light transmitted through the first filter and the second fibrous filter.

18. The device of claim 1, wherein the at least one light source is an LED.

19. The device of claim 1, further comprising a flow measurement and flow control device.

20. The device of claim 17, further comprising an analog to digital converter (ADC) and a microcontroller unit (MCU), wherein the analog voltage measurements form the photodiodes are digitized using the ADC and processed by the MCU.

* * * * *